US00PP36551P2

(12) United States Plant Patent
Shipley

(10) Patent No.: US PP36,551 P2
(45) Date of Patent: Mar. 18, 2025

(54) ***HESPERALOE PARVIFLORA* PLANT NAMED 'Little Miss Sunshine'**

(50) Latin Name: *Hesperaloe parviflora*
Varietal Denomination: Little Miss Sunshine

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 22 days.

(21) Appl. No.: 18/445,794

(22) Filed: Feb. 5, 2024

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1

CPC ... A01H 5/02; A01H 5/12; A01H 5/00; A01H 6/00

See application file for complete search history.

(56) References Cited

PUBLICATIONS

Flora of North America for *Hesperaloe parviflora* 2020, retrieved on Jun. 13, 2024 at http://dev.floranorthamerica.org/Hesperaloe_parviflora, 6 pp. (Year: 2020).*

Mountain States Wholesale Nursery for *Hesperaloe* x 'MSWNIvory Swan' retrieved on Jun. 13, 2024 at https://mswn.com/wp-content/uploads/2021/03/Hesperaloe-XMSWNIvory-Swan-Nite-Lights%C2%AE.pdf, one page. (Year: 2021).*

* cited by examiner

*Primary Examiner* — June Hwu

(57) ABSTRACT

A new and distinct *Hesperaloe parviflora* plant named 'Little Miss Sunshine' is characterized by a compact, upright, formal, semidwarf growth form with upright inflorescences bearing tubular yellow flowers.

4 Drawing Sheets

Latin name: *Hesperaloe parviflora.*
Varietal denomination: 'Little Miss Sunshine'.

BACKGROUND OF THE INVENTION

The present invention relates to a new and distinct cultivar of *Hesperaloe parviflora*. The cultivar originated as part of an ongoing breeding program as a seedling which arose from a proprietary *Hesperaloe parviflora* hybrid breeding line. The female parent was a yellow flowered *Hesperaloe parviflora* hybrid and as the breeding line is not subject to controlled pollination and is open pollinated by a variety of nearby *Hesperaloes* such that the male parent is not known. One of the seedlings grew as an unusually dense and uniform cluster of rosettes, the overall size of which was semidwarfed compared to common existing *Hesperaloe parviflora* cultivars and its female parent. The plant produces numerous inflorescences of moderate size bearing yellow flowers and is the object of this application.

SUMMARY OF THE INVENTION

Among the features that distinguish the new *Hesperaloe* cultivar from all other available and commercial varieties of *Hesperaloe parviflora* known to the inventor are the following combination of characteristics: plant has a compact, upright, formal, semidwarf growth form and bears upright inflorescences with tubular yellow (4C) flowers.

'Little Miss Sunshine' is propagated by tissue culture by an independent laboratory located in Portland, Oregon.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate 'Little Miss Sunshine' growing near Sahuarita, Arizona, depicted in color as nearly correct as it is possible to make in a color illustration of the character.

DETAILED PLANT DESCRIPTION

Figure 1:
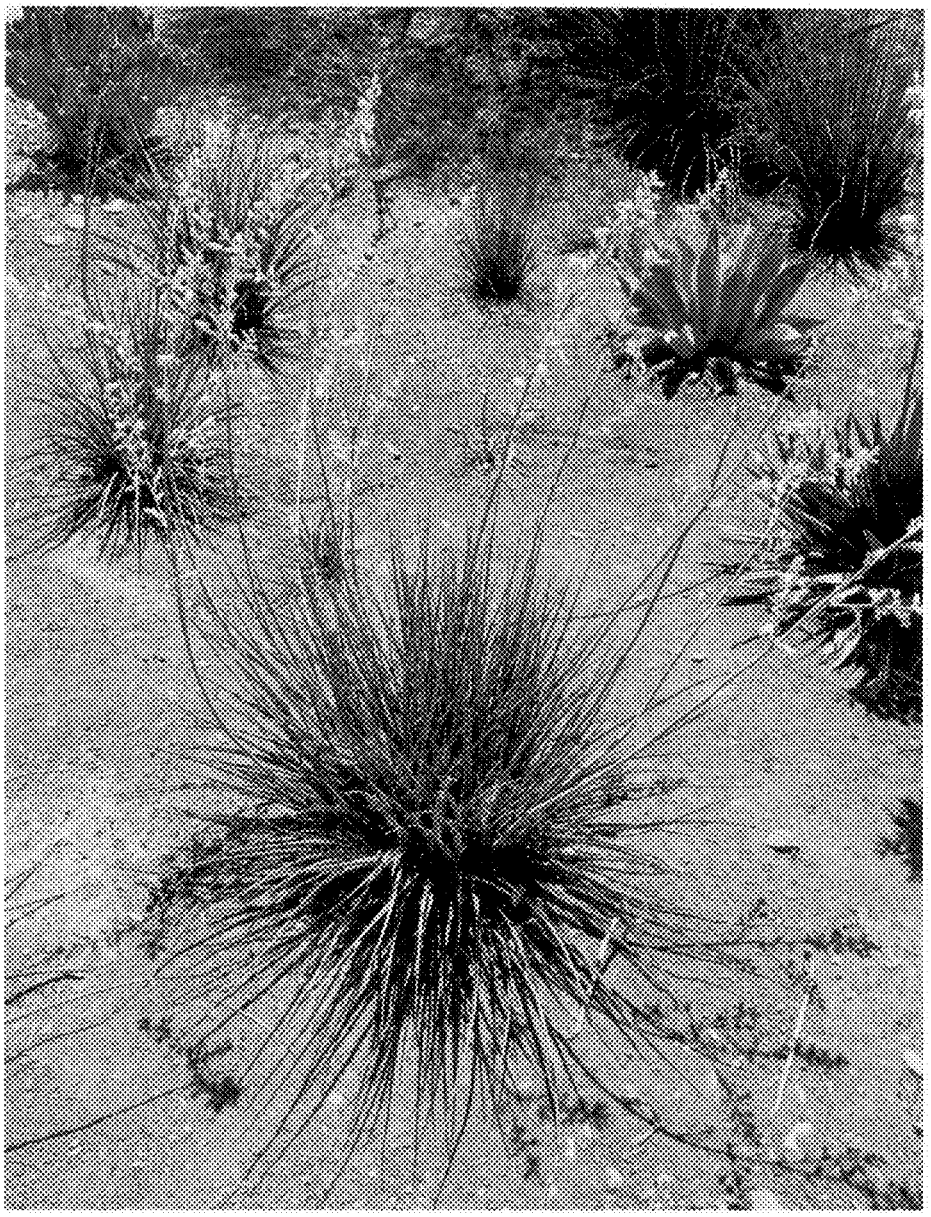
FIG. 1 shows the original *Hesperaloe parviflora* 'Little Miss Sunshine' in bloom at age 4 years growing at a commercial nursery near Sahuarita, Arizona.
Figure 2:
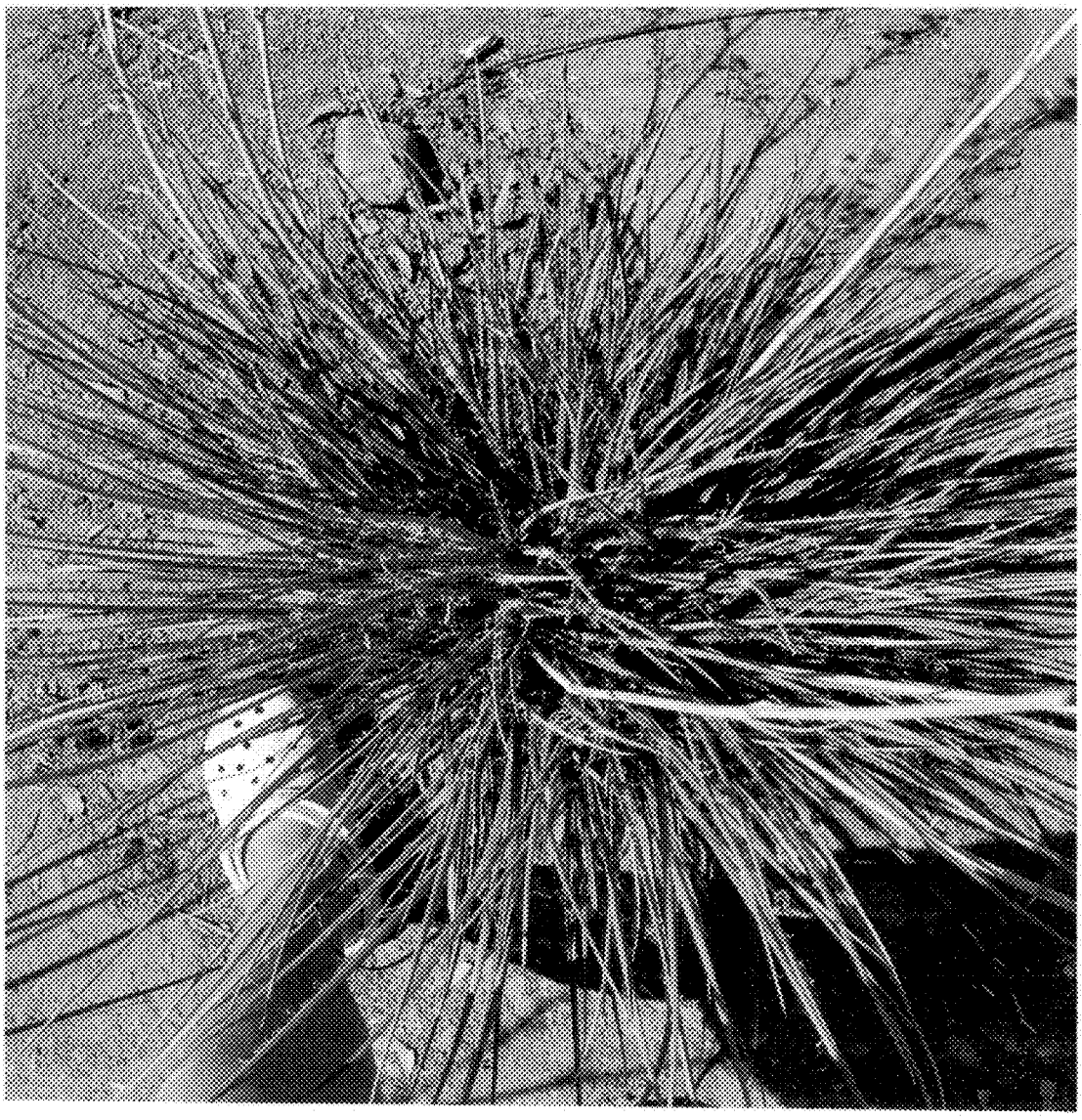
FIG. 2 illustrates the form of the vegetative portion of 'Little Miss Sunshine'.
Figure 3:
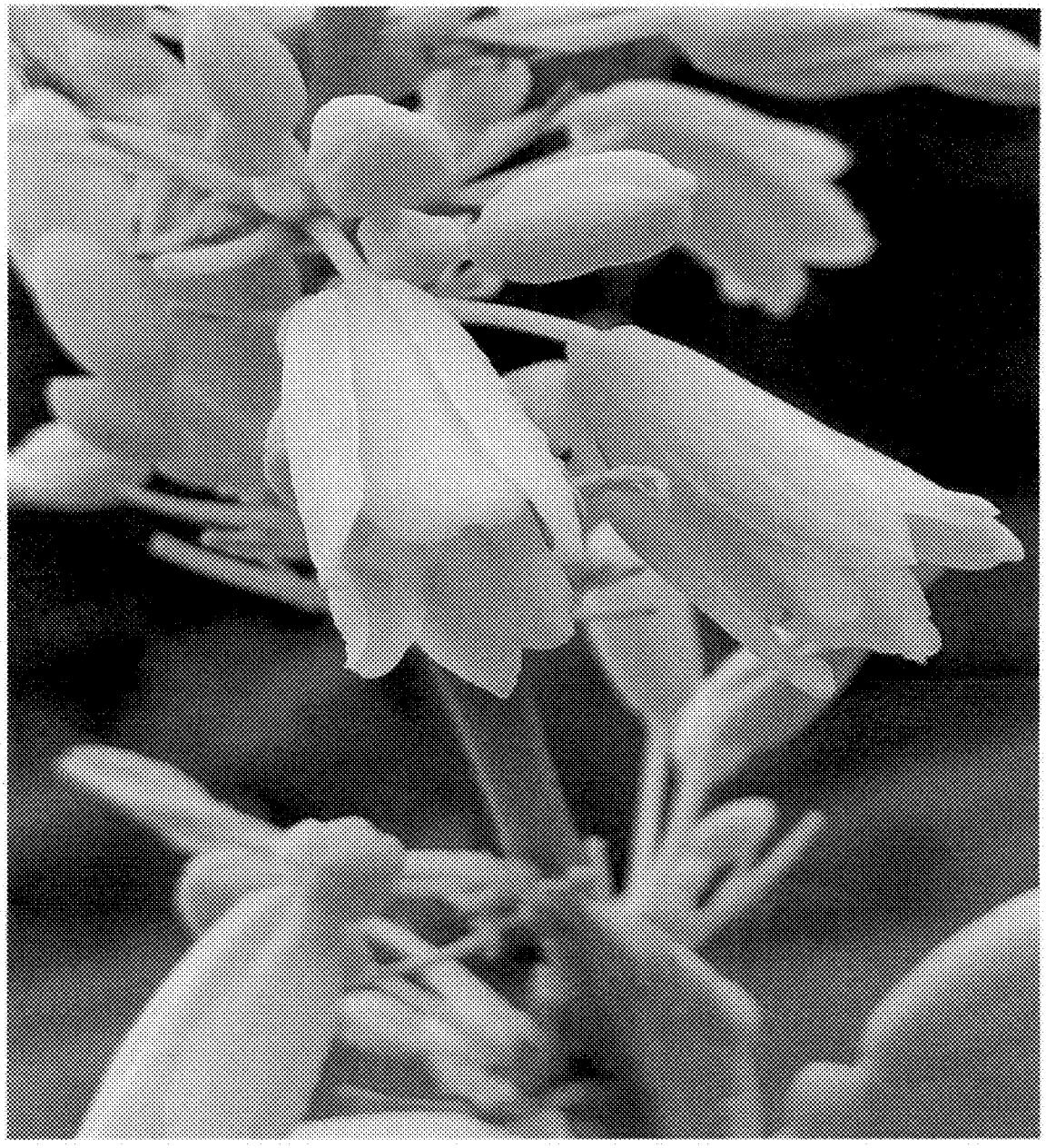
FIG. 3 shows the flowers of 'Little Miss Sunshine'.
Figure 4:
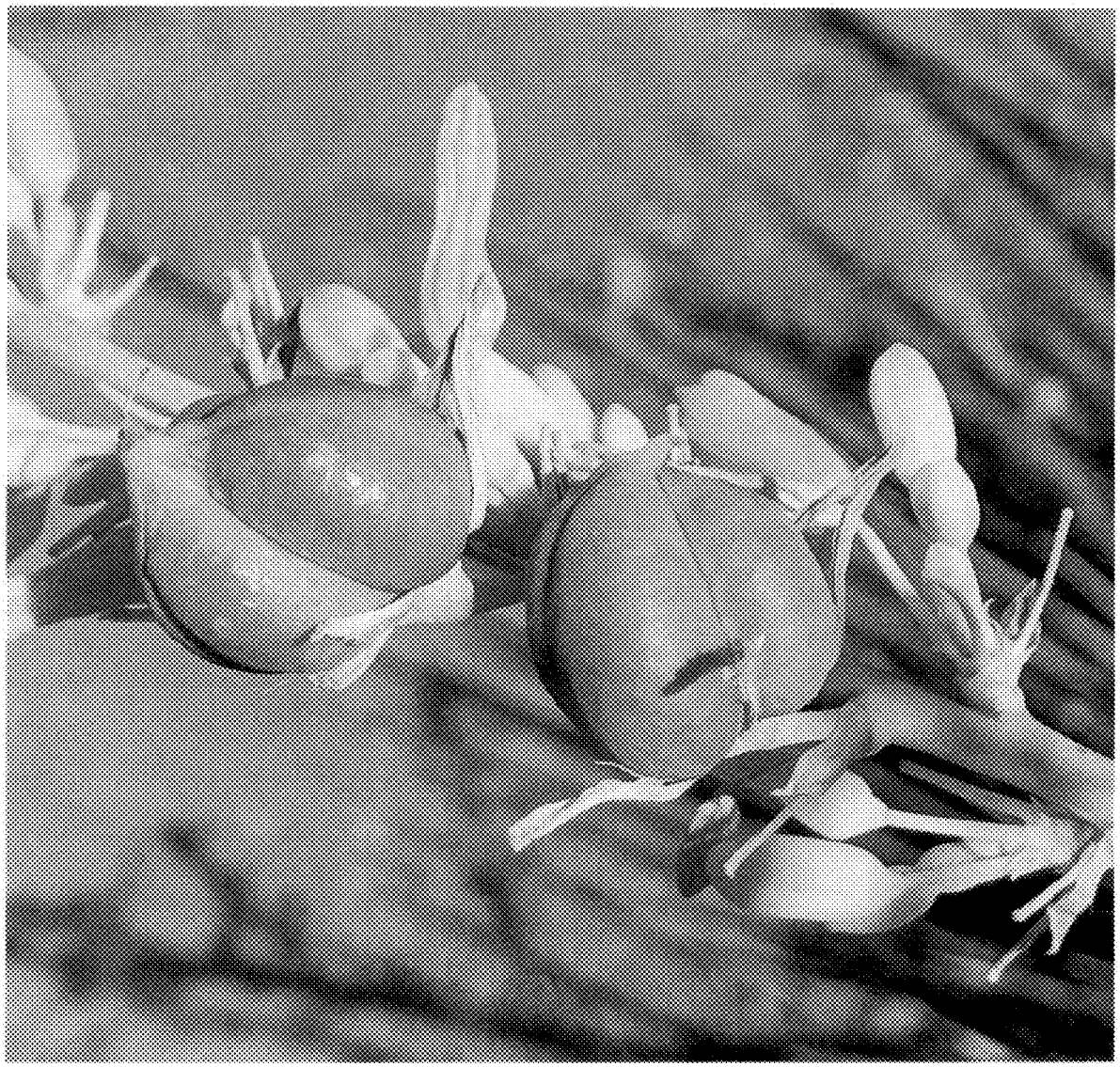
FIG. 4 shows the nearly mature fruits of 'Little Miss Sunshine'.

The following is a detailed description of the new *Hesperaloe parviflora* 'Little Miss Sunshine' plant based upon the original 'Little Miss Sunshine' aged 4 years growing near Sahuarita, Arizona.

The color descriptions are based upon the $5^{th}$ edition R.H.S. Colour Chart, copyright 2007. Color names other than common usage are as listed in *COLOR Universal Language and Dictionary of Names,* by Kenneth L. Kelly and Deane B. Judd; National Bureau of Standards special publication 440. Washington, D.C.: U.S. Department of Commerce, National Bureau of Standards, December 1976.

Plant is a strongly clustering dense rosette semi-succulent long lived perennial with dark green, narrow, thickened leaves. Flowers are produced on upright, slightly spreading spicate panicles which grow up to about 4.5 feet long. 'Little Miss Sunshine' is hardy to −20° F., USDA hardiness zone 5. No disease or insect problems were noted.

At age 4 years under irrigation near Sahuarita, Arizona the plant measures 1.5' tall×3' wide excluding the inflorescences. The plant is a dense cluster of succulent rosettes with approximately 30 rosettes connected to each other below ground level, each with from 8-16 leaves. The flowering is terminal, after which the flowering rosettes cease apical growth and produce offset rosettes. The plant had 12 flower stalks (inflorescences) in 2023, each with 2 to 4 side branches. In bloom the plant measures 4.5' tall×4-6' wide. The plant is fertile and produces fruit and viable seeds.

Leaves vary in length from 33-62 cm in length. The described example was 51 cm long. At the midpoint of this leaf the leaf measured 8 mm wide×7.5 mm thick. The leaves are clasping at the base, fibrous internally, semisucculent and stiff. Leaves other than the basal portion of the leaf are linear, adaxially curled from the leaf edges, glabrous excluding the margins and the distal 6 cm, finely striate the full length of the leaf (the striations more easily seen on the adaxial than the abaxial surface), with the surface scabrous on both sides of the distal ½ of the leaf, the leaf gradually tapers from the base to the acute apex, which is not sharp. The clasping portion of the leaf measures 35 mm wide×3 mm thick, color 155A, both surfaces. The color transitions abruptly to 137A on both surfaces at 7 cm from the leaf base on the adaxial surface and at 4 cm on the abaxial surface. The leaf measures 10 mm wide×7.5 mm thick at the point of the adaxial transition. The remainder of the leaf appears to be 137A visually, but the surface is comprised of microscopically striate alternating bands varying from 50-150μ wide, the striations colored 138D and 136A. The midpoint of the leaf measures 8 mm wide×7.5 mm thick. The leaf margins are irregularly lined with erratic, often branched fibers up to 8 cm long colored N155A. The fibers are present from the edges of the clasping base up to just below 6 cm from the leaf apex. The hairs are of low strength and become caducous with age. The terminal 6 cm of the leaf is microscopically denticulate.

Flowering of 'Little Miss Sunshine' occurs from mid-April through the end of May at the Sahuarita, Arizona location. Individual flowers open at night and close late the following day. The closed flowers do not reopen. The spent flowers fall away within a few days if the fruit does not set. On successful fruits the outer flower parts dry and persist at the fruit base until the fruit matures.

The inflorescence is a spicate panicle 4.0-4.5' long produced from the apex of the primary axis of a mature vegetative rosette. Each inflorescence has 2-4 alternate branches which have alternating fruiting spurs in addition to the main flowering axis. Most flowering occurs on the upper half of the inflorescence. The inflorescence examined had 2 fruiting branches. The inflorescence peduncle is terete and measures 7.5 mm in diameter at the base, color 155A. Most of the inflorescence is faintly striate, glaucous and colored 145A. The color of the peduncle transitions gradually from the base to the predominant color (145A) below the first inflorescence bract. This clasping bract is attached 12 cm above the base and measures 9.5 cm long×1.8 cm wide, is triangular and colored 145A. The bract basal margin is papery, 2-3 mm wide basally tapering to zero 7 mm above the base, the interior (axial) edge colored 199B, the rest colored 197D. The bract apex is enrolled adaxially. The bract is glabrous and weakly glaucous, the margins entire. The second inflorescence bract is attached 35 cm above the peduncle base, clasping, triangular, measuring 5 cm long× 1.9 cm wide. Bract 2 is similar in form and color to bract 1 except the apical 2 cm are dry and colored 199B. Bract 3 is attached to the peduncle 55 cm above the base, measuring 1.7 cm wide at its clasping base and 3.5 cm long, triangular, colored 145A. The apex is dried back 2.9 cm, color 164D. An abortive, dried flowering branch is present inside bract 3, color 164D. Bract 4 is the first successful flowering branch bract, attached 73 cm above the peduncle base. This bract measures 1.6 cm wide at the clasping base×1.6 cm long. The entire bract is dried and brittle with the tip missing, color 164D. Both the flowering branches and the main axis above bract 4 produce alternate fruiting spurs (shortened spikes). The younger portions of the inflorescence transition gradually from 1D to 145A with maturity. The lower spur bracts are broadly ovate in shape with acuminate apices. The basal bracts measure 8 mm long×7 mm wide, color closest to 199C. The upper spur bracts measure 4 mm long×4 mm wide and are triangular, color 199A. Bracts transition in shape and color gradually from the basal to the upper ones. All the bracts are glabrous with entire margins. The spur bracts are dry and quite brittle, and most are broken or missing by fruit maturity.

Each spur produces from 2-8 flowers. The dry flower pedicels persist on the spurs after the flowers have fallen. The spurs excluding the pedicels measure 3-4 mm wide×3-4 mm long. The apical spurs produce fewer flowers than the basal ones.

The mature buds of 'Little Miss Sunshine' are ellipsoid to slightly obovoid in shape, glabrous and glaucous, measuring 15-18 mm long×6-7 mm in diameter and are strongly rounded triangular in cross section. The color is 4C. Pedicels are terete, measuring 11-13 mm long×1 mm in diameter; glaucous and colored 160D. Flowers are actinomorphic, very nectiferous, with 3 glabrous outer tepals and 3 glabrous inner tepals (both fused with the receptacle), which are similar in appearance and color, except the outer tepals are slightly narrower than the inner tepals. The open, highly nectiferous flowers are tubular with a slight flare at the apex, measuring 20 mm long×10 mm wide at the widest point. The flowers are uniformly colored 4C, glaucous externally. There is abscission layer at the pedicel/receptacle attachment. The receptacle measures 3.5 mm wide at the apical portion and 1.2 mm at the pedicel attachment. Receptacle length is 3.5 mm. The apical portion where all the flower parts are fused is discoid, measuring 3.5 mm in diameter and 1.5 mm thick. Below this portion the receptacle is conical, narrowing to 1.2 mm at the pedicel. Receptacle color is 4D. Outer tepals (3) are petaloid, elliptical in shape, glabrous, slightly succulent and externally glaucous, measuring 18 mm long×4 mm wide, color 4C, both surfaces. The apex of the outer tepals is slightly acuminate, the base truncate measuring 3 mm wide. The outer tepal margin is entire. The three inner tepals are slightly succulent, oblanceolate and glabrous, measuring 18 mm long×5.5 mm wide, color 4C, both surfaces. The inner tepal apex is broadly acute and rounded. the base is truncate, measuring 1.5 mm wide. Six stamens are attached to the receptacle, each one centered along the axis of an outer or inner tepal. The stamens are 15 mm in length, terete in cross section. The filaments measure 13.5 mm long, gradually tapering from the base to the anthers, basally 1.2 mm in diameter, apically 0.4 mm in diameter. The filaments are colored 155B. The filaments are glabrous. Anthers are dorsifixed near the base, anthers slightly tilted to the attachment side. The anthers dehisce soon after anthesis and are fully dehisced by daybreak. Dehisced anthers measure 1.6 mm long×1 mm wide, colored 15C. Undehisced anthers in mature buds measure 4.2 mm long×1.3 mm wide×1.0 mm thick, colored 11A. Pollen is ellipsoid, colored 15C and measures 80μ×30μ.

The pistil measures 11 mm long and is widest at the ovary. The superior ovary measures 3.5 mm long×2.2 mm in diameter. The ovary contains 3 carpels, color 4D, broadly ellipsoid in shape, weakly rounded triangular in cross section, The style, color 155A, is 7.5 mm long and gradually tapers from 1.9 mm in diameter at the base to 0.9 mm just below the stigma. The stigma is truncate, color 4D. The stigma measures 0.9 mm across and 0.1 mm thick.

Nearly mature fruits (close to mature size but seeds with immature characteristics, particularly color, which is generally dark to black for this species) are glaucous, glabrous, color 139C, longitudinally 3 grooved obturbinate is shape, measuring 18-20 mm in length and 16-18 mm in diameter. The pedicel on nearly mature fruit measures 10-11 mm long and 1.8 mm in diameter, color 145C. The pedicel surface is glaucous and glabrous.

Immature seeds are half moon shaped and sit inside each of the 3 carpels with flat edges facing each other in 2 rows of about 15 seeds/row (30/carpel, 90/fruit). The seeds measure 5-8 mm long×2-3 mm wide×1-2 mm thick. The seeds at this stage of development were colored 155D.

Mature seeds were not available for this description. The seed surface is smooth and glabrous. The thinnest seeds are located toward the middle of the fruit are largest in width and length while the thickest seeds from the fruit base and apex regions have the smallest length×width measurements resulting in seeds throughout the fruit containing similar volumes.

COMPARISONS TO RELATED . . .

Compared to the female parent, 'Little Miss Sunshine' is a smaller, more formal looking plant. The vegetative portion has more upright and densely packed rosettes and the inflorescences are more upright and uniform as well.

The male parent cannot be determined as this hybrid resulted from open pollination from several different possible source plants.

Compared to *Hesperaloe parviflora* 'Yellow', unpatented, 'Little Miss Sunshine' is a smaller plant with a much greater density and number of rosettes which are upright and uniform. The leaves of 'Little Miss Sunshine' are darker green than 'Yellow'. The flowering form of 'Yellow' is sprawling while that of 'Little Miss Sunshine' is upright.

Compared to *Hesperaloe parviflora* 'Desert Flamenco' (not patented), 'Little Miss Sunshine' has yellow flowers while those of 'Desert Flamenco' are bicolored pink/light orange. Also 'Desert Flamenco' has a more highly branched inflorescence than 'Little Miss Sunshine'. The plant of 'Desert Flamenco' is larger than that of 'Little Miss Sunshine'.

*Hesperaloe campanulata* 'MSWNNuevo Leon' (U.S. Plant Pat. No. 32,069) is compared since *Hesperaloe campanulata* and *parviflora* are similar and related species. The two cultivars are quite easily separated as 'MSWNNuevo Leon' is a much larger plant with inflorescences much more branched and more than twice the size of 'Little Miss Sunshine'. Also 'MSWNNuevo Leon' has pink flowers compared to yellow flowers on 'Little Miss Sunshine'.

*Hesperaloe parviflora* X *funifera* 'MSWNIvory Swan' (not patented) is a much larger plant than 'Little Miss Sunshine' with creamy white, rather than yellow flowers.

*Hesperaloe parviflora* 'Coral Glow' (U.S. Plant Pat. No. 29,626) has bicolored peach/yellow flowers compared to the yellow flowers of 'Little Miss Sunshine'.

*Hesperaloe parviflora* 'PERPA' (U.S. Plant Pat. No. 21,729) (BRAKELIGHTS™) has broadly opening red flowers compared to tubular yellow flowers on 'Little Miss Sunshine'. 'Little Miss Sunshine' is more vigorous than 'PERPA' and has taller, more upright inflorescences. 'Little Miss Sunshine' produces fruits and seeds while 'PERPA' does not.

*Hesperaloe parviflora* 'MSWNPered' (U.S. Plant Pat. No. 28,910), (SANDIA GLOW™) has red flowers while those of 'Little Miss Sunshine' are yellow.

*Hesperaloe parviflora* 'MSWNPerma' (U.S. Plant Pat. No. 28,909) (DESERT DUSK™) has purple peduncles and red/purple flowers compared to green peduncles and yellow flowers on 'Little Miss Sunshine'.

The inflorescence of 'MSWNPerma' is about half the length of that of 'Little Miss Sunshine'. *Hesperaloe parviflora* 'Stop Lights' (U.S. Plant Pat. No. 34,195) has red flowers compared to yellow flowers on 'Little Miss Sunshine'. 'Little Miss Sunshine' has a denser, more upright growth form on both the plant and the inflorescence compared to 'Stop Lights'.

*Hesperaloe funifera* X *parviflora* 'Perfu' (U.S. Plant Pat. No. 21,728), (PINK PARADE™) plants are roughly twice the size of 'Little Miss Sunshine' and have pink flowers compared to yellow on 'Little Miss Sunshine'.

I claim:

1. A new and distinct *Hesperaloe parviflora* plant named 'Little Miss Sunshine' substantially as described and illustrated herein.

* * * * *